United States Patent [19]

Ok et al.

[11] Patent Number: 5,220,001
[45] Date of Patent: Jun. 15, 1993

[54] ANTHRACYCLINE GLYCOSIDE DERIVATIVES

[75] Inventors: Kwang D. Ok; Jeong B. Park; Moon S. Kim, all of Seoul, Rep. of Korea

[73] Assignees: Zaidan Hojim Biseibutsu Dong-A Pharm Co., Seoul, Rep. of Korea; Kagaku Kenkyukai, Tokyo, Japan

[21] Appl. No.: 600,708

[22] Filed: Oct. 22, 1990

[30] Foreign Application Priority Data

Oct. 25, 1989 [KR] Rep. of Korea .................... 89-15375
Oct. 13, 1990 [KR] Rep. of Korea .................... 90-16213

[51] Int. Cl.$^5$ ............................................. C07H 15/24
[52] U.S. Cl. ......................................... 536/6.4; 514/34
[58] Field of Search ............................. 536/6.4; 514/34

[56] References Cited

U.S. PATENT DOCUMENTS

| | | | |
|---|---|---|---|
| 3,590,028 | 6/1971 | Arcamone et al. | 260/210 |
| 3,997,662 | 12/1976 | Pinnert et al. | 424/119 |
| 4,870,058 | 9/1989 | Morton et al. | 514/34 |

Primary Examiner—Johnnie R. Brown
Assistant Examiner—Elli Peselev
Attorney, Agent, or Firm—Birch, Stewart, Kolasch & Birch

[57] ABSTRACT

A compound of the following formula (I) exhibits an excellent antitumor activity

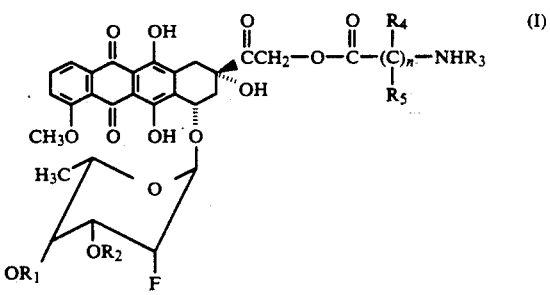

wherein $R_1$ and $R_2$ represent hydrogen atom, respectively, or include both straight or branch chain alkylidene group of 1–10 carbon atoms; $R_3$ represents hydrogen atoms, straight and branch chain alkyl group of 1–10 carbon atoms, straight or branch chain alkyloxycarbonyl group of 1–10 carbon atoms or 3-membered to 6-membered heterocycle containing one nitrogen atom with adjacent alkylene group such as pyrrolidine and N-butoxycarbonyl-pyrrolidine; $R_4$ and $R_5$ represent hydrogen atom or alkyl group of 1–5 carbon atoms, respectively; and n represents 0 or an integer of 1–10, or pharmaceutically acceptable salt thereof.

1 Claim, No Drawings

ANTHRACYCLINE GLYCOSIDE DERIVATIVES

BACKGROUND OF THE INVENTION

1. Field of the Invention

The present invention relates to a novel anthracycline glycoside derivatives of the following formula (I):

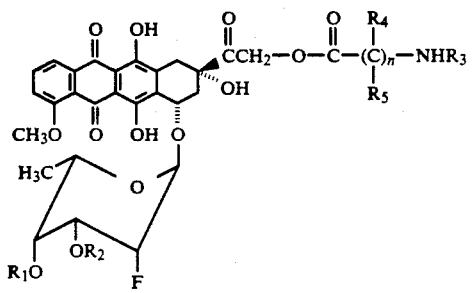

wherein $R_1$ and $R_2$ represent hydrogen atom, respectivelly, or include both straight or branch chain alkylidene group of 1-10 carbon atoms; $R_3$ represents hydrogen atom, straight or branch chain alkyl group of 1-10 carbon atoms, straight or branch chain alkyl-oxycarbonyl group of 1-10 carbon atoms or 3-membered to 6-membered heterocycle containing one nitrogen atom with adjacent alkylene group such as pyrrolidine and N-(t-butoxycarbonyl-pyrrolidine; $R_4$ and $R_5$ represent hydrogen atom or alkyl group of 1-5 carbon atoms, respectively; and n represents 0 or an integer of 1-10, or pharmaceutically acceptable salt thereof.

2. Description of the Prior Art

As the antibiotics of anthracycline series, daunorubicin disclosed in U.S. Pat. No. 3,997,662 and doxorubicin disclosed in U.S. Pat. No. 3,590,028 were obtained from the fermented broth of Actinomyces species. The anthracyclines have a broad spectrum antitumor activity and have been used as chemotherapeutics against malignant tumors.

The formula (A) of the above anthracyclines is as follows:

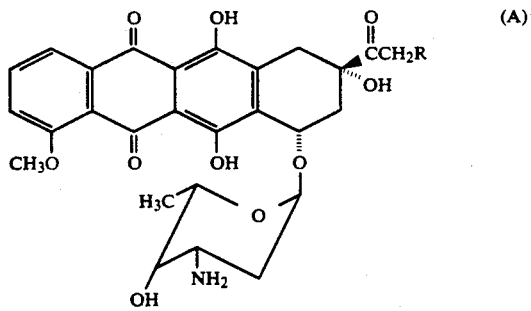

wherein R represents hydrogen atom or hydroxyl group.

In addition, the formula (B) of 2-fluoro-substituted anthracycline derivative disclosed in Japanese Patent Laid Open Publication No. Sho 62-145,097 is as follows:

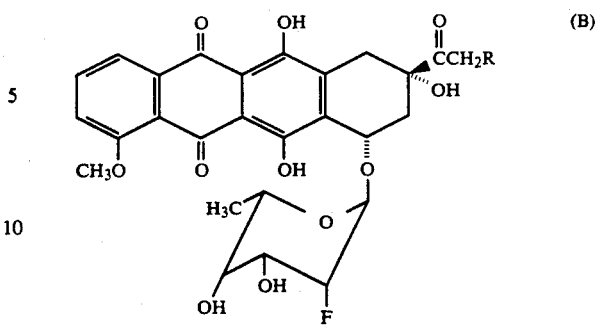

wherein R represents hydrogen atom or hydroxyl group.

Moreover, the formula (C) of a soluble derivative of the above-identified compound (B) disclosed in Japanese Patent Laid Open Publication No. Sho 63-141,992 is as follows:

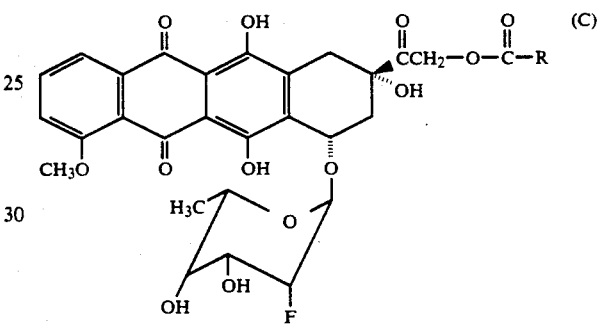

wherein R represents $-(CH_2)_mH$ (m represents 0 or an integer of 1 to 6) or $-(CH_2)_nCOOH$ (n represents 0 or an integer of 1 to 10).

However, since the above-identified anthracyclines exhibit certain undesirable side effects, they have had a limited usefulness of anthracyclines such as daunorubicin and doxorubicin derivatives. One of their more serious side effects is their cardiotoxicity which severely restricts the dosages and the frequency with which they can be administered and in turn, limits their overall effectiveness as a chemotherapeutic agent against malignant tumors. And one of the other disadvantages of the above known compounds is that they have relatively low solubility in water. In view of the low water solubility, these compounds are difficult to administer in amounts which would be effective in the treatment of some cancers.

SUMMARY OF THE INVENTION

Accordingly, it is an object of the present invention to provide a novel anthracycline glycoside derivative represented by the above formula (1) or pharmaceutically acceptable salt thereof.

Another object of the present invention is to provide a process for the preparation of the anthracycline glycoside derivative represented by the formula (I) or pharmaceutically acceptable salt thereof.

Other objects and further scope of applicability of the present invention will become apparent from the detailed description given hereinafter. It should be understood, however, that the detailed description and specific examples, while indicating preferred embodiments of the invention, are given by way of illustration only, since various changes and modifications within the spirit and scope of the invention will become apparent to those skilled in the art from this detailed description.

DESCRIPTION OF THE PREFERRED EMBODIMENTS

The present invention relates to a novel anthracycline glycoside derivatives represented by the following formula (I) or pharmaceutically acceptable salt thereof which exhibit good antitumor activities with low toxicity and good solubility in isotonic water or even in neutral water

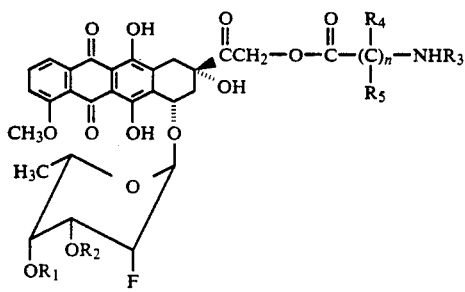

wherein $R_1$ and $R_2$ represent hydrogen atom, respectively, or include both straight and branch chain alkylidene group of 1–10 carbon atoms; $R_3$ represents hydrogen atom, straight or branch chain alkyl group of 1–10 carbon atoms, straight or branch chain alkyloxycarbonyl group of 1–10 carbon atoms or 3-membered to 6-membered heterocycle containing one nitrogen atom with adjacent alkylene group such as pyrrolidine and N-(t-butoxycarbonyl-pyrrolidine; $R_4$ and $R_5$ represent hydrogen atom or alkyl group of 1–5 carbon atoms, respectively; and n represents 0 or an integer of 1–10, or pharmaceutically acceptable salt thereof.

The pharmaceutically acceptable salts mentioned in the present invention are inorganic acid addition salts such as halide, phosphate, sulfate, nitrate, and the like. The organic acid addition salts are acetate, methanesulfonate, benzenesulfonate and p-toluenesulfonate, and the like. Anthracycline glycoside derivatives of the formula (I) or the salts thereof exhibit significant antitumor activity in animals with less toxicity than the conventional derivatives mentioned in the above.

The process for the preparation of anthracycline glycoside derivatives of the formula (I) comprises reacting a compound of the following formula (II) in which the hydroxyl groups in 3', 4'-positions may be protected

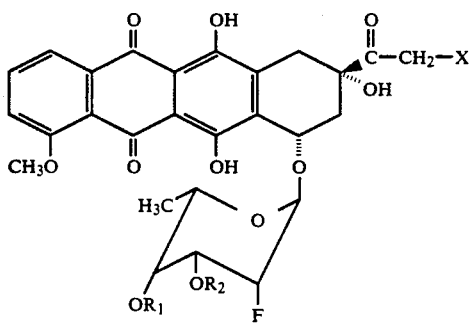

wherein $R_1$ and $R_2$ are the same as defined in the above and X represents bromine, chlorine or iodine atom, with a compound of the following formula (III)

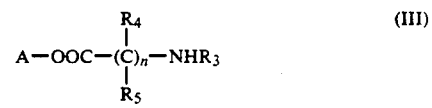

wherein $R_3$, $R_4$, $R_5$ and n are the same as defined above and A represents hydrogen atom or an alkali metal.

The protecting groups in the 3', 4'-positions and amino protecting group are removed, and then the obtained compound is converted to the pharmaceutically acceptable acid addition salt, if necessary. However, the salt of the compound of the formula (I) can be easily prepared int he process of the above deprotecting reaction. For example, in the process for the preparation of the compound of the formula (I) or its salt, when X represents bromine and hydroxyl groups in 3', 4'-positions are protected by isopropylidene, the reaction process is represented by the following reaction scheme:

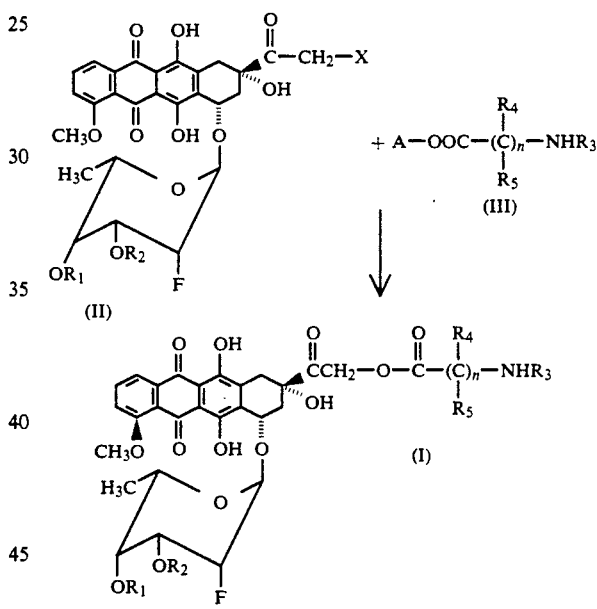

wherein $R_1$, $R_2$, $R_3$, $R_4$, $R_5$, n and A are the same as defined above.

The reaction process between the compound of the formula (II) and the compound of the formula (III) is carried out in a conventional solvent such as, for example, water; alcohol, e.g. ethanol; nitriles, e.g. acetonitrile; ketones, e.g. acetone or methylethylketone; cyclic or aromatic amines, e.g. pyridine, pyrrolidine or pyrroline; aromatic hydrocarbones, e.g. benzene, toluene; ethers, e.g. dioxane, tetrahydrofurane; halogenated hydrocarbons, e.g. chloroform, dichloromethane; and amides e.g. formamide, dimthylformamide, dimethylacetamide or mixed solvents thereof. The reaction process is carried out between 0° C. boiling point of the solvent used for 30 minutes–48 hours.

In carrying out the present reaction process, hydroxyl groups can be protected before the reaction and the protected hydroxyl groups can be deprotected after the reaction. As a protecting group, straight or branch chain alkylene group can be used.

The starting compound of the formula (II) of the present invention can be obtained from the compound described in the Japanese Patent Laid Open Publication No. Sho 62-145,097.

If it is required that the hydroxyl groups of the compound of the formula (I) are deprotected, the protected compound is deprotected with acid such as formic acid, acetic acid, hydrochloric acid, sulfuric acid or phosphoric acid. The amino protecting group can be easily removed, too.

Solvent which may be used in the deprotecting reaction is non-protonic solvent such as water, alcohol, DMF, DMSO, dioxane, ether, chloroform, THF, dichloromethane or the mixtures thereof. The deprotecting reaction can be carried out between 0° C.–boiling point of solvent used in the reaction. The compound of the formula (I) may be converted to the salt thereof in a conventional organic solvent such as alcohol, dichloromethane, ether, chloroform, THF, or dioxane.

The present invention will now be described in more detail in connection with the following examples which should be considered as being exemplary and not limiting the present invention.

EXAMPLE 1

Preparation of 7-0-(2,6-dideoxy-2-fluoro-3,4--O-isopropylidene-α-L-talopyranosyl)-adriamycinone 14-0-[N-(t-butyloxycarbonyl (Boc)) glycinate].

1.5g of sodium N-t-butyloxycarbonyl-glycinate was added to a solution of 180 mg of 14-bromo-7-0-(2,6-dideoxy-2-fluoro-3,4-0-isopropylidene-α-L-talopyranosyl)daunomycinone in aqueous aceton (7:26, 33ml). The mixture was stirred for 20 hours and was distilled under reduced pressure to obtain a residue. The residue was extracted by chloroform washed with water and saturated NaCl solution successively and was dried in vacuo. The residue was purified by silicagel chromatography (eluting solvent: mixed solvent of chloroform: methanol=20:1) to obtain 121 mg of the compound (59%).

MP: 142°–143.5° C.
NMR (CDCl$_3$, ppm, specific peak).
13.7, 13.1 (OH×2),
5.53 (d,d, 1H, H-1', $J_{H-1'-H-2'}$=5.6 Hz, $^3J_{H-1'-F}$=14Hz),
4.01 (s, 3H, OCH$_3$),
1.55 (s, 3H, CH$_3$),
1.32 (s, 3H, CH$_3$),
1.30 (d, 3H, CH$_3$, $J_{CH_3\text{-}H\text{-}5'}$=6.4 Hz),
1.44 (s, 9H, t-butyl).

EXAMPLE 2

Preparation of 7-0-(2,6-dideoxy-2-fluoro-α-L-talopyranosyl)-adriamycinone 14-0-glycinate HCl salt The compound (100 mg) obtained in the Example 1 was dissolved in 10 ml of 80% acetic acid solution and was stirred at 80° C. for 3 hours. Solvent was distilled under reduced pressure to obtain a residue. The residue was chromatographed on a column of silica gel (eluting solvent; chloroform: methanol-5:1) to obtain 7-0-(2,6-dideoxy-2-fluoro-α-L-talopyranosyl)-adriamycinone 14-0-glycinate. The obtained compound was dissolved in small amount of dichloromethane. Saturated HCl-ether solution was dropwise added to the solution to obtain a red solid. The obtained red solid was washed with ether, centrifuged and dried to obtain the title compound as HCl salt (48 mg, 56%).

MP: 179°–185° C.
NMR(CDCl$_3$, ppm, specific peak),
14.0, 13.2 (s, each 1H, OH×2),
8.3 (brs, 3H, —NH$_3$Cl),
7.9 (m, 2H, aromatic proton),
7.6 (m. 1H, aromatic proton),
4.0 (m, 5H, OCH$_3$, Co—CH$_2$—N),
1.2 (d, 3H, CH$_3$, $J_{CH^3\text{-}H\text{-}5'}$=6.4 Hz).

EXAMPLE 3

Preparation of 7-0-(2,6-dideoxy-2-fluoro-α-L-talopyranosyl)adriamycinone 14-0-glycinate HCl salt.

The compound (120 mg) obtained in the Example 1 was dissolved in 1.5 ml of chloroform and 15 ml of methanol was added thereto. 12 ml of saturated HCl-ether solution was added thereto and the mixture was stirred for 4 hours. After the completion of reaction, a considerable amount of solvent was distilled to obtain a residue. Ether was added to the residue to obtain a solid. The solid was filtered and dried to obtain the compound (84 mg, 80%).

EXAMPLE 4

Preparation of 7-0-(2,6-dideoxy-2-fluoro-3,4-0-isopropylidene- α-L-talopyranosyl)-adriamycinone 14-0-[N-(t-butyloxycarbonyl(Boc))-β-alaninate]

200 g of 14-bromo-7-0-(2,6-dideoxy-2-fluoro-3,4-isopropylidene-α-L-talopyranosyl) daunomycinone was reacted with 634 mg of sodium N-(t-butyloxycarbonyl)-β-alaninate by the analogous method of Example 1 to obtain the compound (144 mg, 62%) as a red solid. Mixture solvent of benzene and acetone (4:1) was used as eluting solvent for silica gel chromatography.

MP : 138°–140.5° C.
NMR(CDCl$_3$, ppm, specific peak), 13.8, 13.2(s, each 1H, OH×2), 5.5(d,d, 1H, H-1', $J_{H-1'-H-2'}$=5.6 Hz, $J_{H-1'-F}$=13.8 Hz), 4.1(s, 3H, OCH$_3$) 1.5, 1.4 (s, each 3H, CH$_3$×2), 1.3(d, 3H, CH$_3$, $J_{CH_3\text{-}H\text{-}5'}$=6.4 Hz), 1.4(s, 9H, t-butyl).

EXAMPLE 5

Preparation of 7-0-(2,6-dideoxy-2-fluoro-α-L-talopyranosyl)adriamycinone 14-0-β-alaninate HCl salt.

The compound (140 mg) obtained in Example 4 was treated by the analogous method of Example 3 to obtain the title compound (92 mg, 76%).

MP : 195°–200° C.
NMR(DMSO-d$_6$, ppm, specific peak), 14.0, 13.2 (s, each 1H, OH×2), 7.9 (m, 5H, —NH$_3$Cl, 2H (aromatic proton)), 7.6 (m, 1H, 1H (aromatic proton)), 3.9 (s, 3H, OCH$_3$), 1.1 (d, 3H, CH$_3$, $J_{CH_3\text{-}H\text{-}5'}$=6.5 Hz).

EXAMPLE 6

Preparation of 7-0-(2,6-dideoxy-3,4-0-isopropylidene-α-L-talopyranosyl)-adriamycinone14-0-[6-(t-butyloxycarbonyl(Boc))-amino hexanoate].

220 mg of 14-bromo-7-0-(2,6-dideoxy-2-fluoro-3,4-0-isopropylidene-α-L-talopyranosyl) daunomycinone was reacted with 900 mg of sodium 6-(t-butyloxycarbonylamino) hexanoate by the analogous method of Example 1 to obtain the title compound (158 mg, 64%) as a red solid. Mixed solvent of benzene and acetone (4:1) was used as eluting solvent for silicagel chromatography.

MP : 130°–132° C.
NMR(CDCl$_3$, ppm, specific peak), 13.8, 13.2 (s, each 1H, OH×2), 5.5 (d,d, 1H, H-1', $J_{H-1'-H-2'}$=5.5 Hz, $J_{H-1'-F}$=13.8 Hz), 4.0 (s, 3H, OCH$_3$), 1.5 (s, 9H, t-butyl), 1.6, 1.5 (s, each 3H, CH$_3$×2), 1.3 (d, 3H, CH$_3$, J$_{CH3-H-5'}$=6.4 Hz).

EXAMPLE 7

Preparation of 7-0-(2,6-dideoxy-2 fluoro-α-L-talopyranosyl)adriamycinone 14-0-(6-aminohexanoate) HCl salt.

The compound (15 mg) obtained in Example 6 was treated by the analogous method of Example 3 to obtain the compound (95 mg, 72%).

MP : 188°–192° C.

NMR(DMSO-d$_6$, ppm, specific peak), 14.0, 13.2 (s, each 1H, OH×2), 7.8 (m, 3H, aromatic proton and amino), 7.6 (m, 3H, aromatic proton and amino), 3.9 (s, 3H, OCH$_3$), 1.3 (s, 6H, —CH$_2$—CH$_2$—CH$_2$—), 1.2 (d, 3H, CH$_3$, J$_{CH3-H5'}$=6.4 Hz).

EXAMPLE 8

Preparation of 7-0-(2,6-dideoxy-2-fluoro-3,4-0-sopropylidene- α-L-talopyranosyl)-adriamycinone 14-0-[N-(t-butyloxycarbonyl)-L-alaninate]

200 mg of 14-bromo-7-0-(2,6-dideoxy-2-fluoro-3,4-0-isopropylidene-L-talopyranosyl)daunomycinone was reacted with 650 mg) by the mg of sodium N-(t-butyloxycarbonyl)-L-alaninate (650 mg) by the analogous method of Example 1 to obtain the title compound (137 mg, 50%) as a red solid. mixture solvent of benzene and acetone 94:1) was used as eluting solvent for silicagel chromatography.

Mp : 148.5°–151.0° C.

NMR (CDCl$_3$, ppm, specific peak), 3.8, 13.2 (s, each 1H, OH×2), 5.5 (d,d, 1H, H-1', J$_{H-1'-H-2'}$=5.6 Hz, J$_{H-1'-F}$=13.8 Hz), 4.1 (s, 3H, OCH$_3$), 1.5, 1.4 (S, EACH 3H, CH×2), 1.3 (D, 3H, CH$_3$, J$_{CH3-H-5'}$=6.5 Hz), 1.5 (d, 3H, CH$_3$, J$_{CH3-CH}$=7.1 Hz),
1.4 (s, 9H, t-butyl).

EXAMPLE 9

Preparation of 7-0-(2,6-dideoxy-2-fluoro-α-L-talopyranosyl)adriamycinone 14-0-L-alaninate HCl salt.

The compound (130 mg) obtained in Example 8 was treated by the analogous method of Example 3 to obtain the compound (90 mg, 80%).

MP : 177°–184° C.

NMR (DMSO-d$_6$, ppm, specific peak), 14.0, 13.2 (s, each 1H, OH×2), 8.5 (br, s, 3H, —NH$_3$Cl), 7.9 (m, 2H, aromatic proton), 7.6 (m, 1H, aromatic proton), 3.9 (s, 3H, OCH$_3$), 1.5 (d, 3H, CH$_3$, J$_{CH3-CH}$=7.1 Hz), 1.3 (d, 3H, CH$_3$, J$_{CH3-H-5'}$=6.5 Hz).

EXAMPLE 10

Preparation of 7-0-(2,6-dideoxy-2-fluoro-3,4-0-isopropylidene- α-L-talopyranosyl)-adriamycinone 14-0-[N-(t-butyloxycarbonyl)-L-valinate]

200 mg of 14-bromo-7-0-(2,6-dideoxy-2-fluoro-3,4-0-isopropylidene-α-L-talopyranosyl)daunomycinone was reacted with 700 mg of sodium N-(t-butyloxycarbonyl)-L-valinate by the analogous method of Example 1 to obtain the compound (145 mg, 60%) as a red solid. Mixture solvent of benzene and acetone (4:1) was used as eluting solvent for the silicagel chromatography.

MP : 137°–139° C.

NMR(CDCl, ppm, specific peak), 13.9, 13.2 (s, each 1H, OH×2), 5.5 (d.d, 1H, H-1', J$_{H-1'-H-2'}$=5.5 Hz, J$_{H-1'-F}$=13.8 Hz), 4.0 (s, 3H, OCH$_3$), 1.4 (s, 9H, t-butyl), 1.3 (d, 3H., Ch$_3$, J$_{CH3-H-5'}$=6.4 Hz), 1.0 (d, d, 6H, —CH(CH$_3$)$_2$).

EXAMPLE 11

Preparation of 7-0-(2,6-dideoxy-2-fluoro-α-L-talopyranosyl)adriamycinone 14-0-L-valinate HCl salt The compound (140 mg) obtained in Example 10 was treated by the analogous method of Example 3 to obtain the compound (90 mg, 74%) as a red solid.

MP : 164°–168° C.

NMR(DMSO-d$_6$, ppm, specific peak), 14.0, 13.2 (s, each 1H, OH×2), 8.4 (br.s., 3H, NH$_3$Cl), 7.9 (m, 2H, aromatic proton), 7.6 (m, 1H, aromatic proton), 4.0 (s, 3H, OCH$_3$), 1,2 (d, 3H, CH$_3$, J$_{CH3-H-5'}$=6.5 Hz), 1.0 (d.d, 6H, —CH(CH$_3$)$_2$).

EXAMPLE 12

Preparation of 7-0-(2,6-dideoxy-2-fluoro-3,4-0-isopropylidene-α-L-talopyranosyl)-adriamycinone 14-0-[N-(t-butyloxycarbonyl)-L-prolinate].

200 mg of 14-bromo-7-0-(2,6-dideoxy-2-fluoro-3,4-0-isopropylidene-α-L-talopyranosyl)daunomycinone and 900 mg of sodium N-(1-butyloxycarbonyl)-L-prolinate (900 mg) were treated by the analogous method of Example 1 to obtain the compound (150 mg, 62%) as a red solid. Mixed solvent of benzene and acetone (4:1) was used as eluting solvent for the silicagel chromatography.

MP : 145.5°–148.5° C.

NMR(CDCl$_3$, ppm, specific peak), 13.8, 13.2 (s, each 1H, OH×2), 5.5 (d, d, 1H, H-1', J$_{H-1'-H-2'}$=5.5 Hz, J$_{H-1'-F}$=13.8 Hz), 4.0 (s, 3H, OCH$_3$), 1.4(s, 9H, t-butyl).

EXAMPLE 13

Preparation of 7-0-(2,6-dideoxy-2-fluoro-α-L-talopyranosyl)adriamycinone 14-0-L-prolinate HCl salt The compound (140 mg) obtained in the Example 12 was treated by the analogous method of Example 9 to obtain the compound (94 mg, 77%) as a red solid.

MP : 180°–185° C.

NMR(DMSO-d$_6$, ppm, specific peak), 14.0, 13.1 (s, each 1H, OH×2), 10.2, 9.1 (2 br.s., each 1H, -NH$_3$Cl), 7.9 (m, 2H, aromatic proton), 7.6 (m, 1H, aromatic proton), 3.9 (s, 3H, OCH$_3$), 1.2 (d, 3H, CH$_3$, J$_{CH3-H-5'}$=6.3 Hz).

Biologic Activity

Experiment 1

The in vivo antitumor activity of the compounds of present invention was studied on DCF$_1$ mice bearing L1210 murine leukemia. Healthy female DCF$_1$ mice were inoculated by intraperitoneal injection with 1×10$^5$ L1210 leukemia cells per animal. The inoculated mice were then treated intraperitoneally on the days 1, 5, 9 beginning on day 1, 24 hours after inoculation of the leukemia cells with various doses of test compounds. Doxorubicin hydrochloride was administered for comparison. All test compounds and doxorubicin hydrochloride were dissolved in filtered (0.22 μm) distilled water. The animals were observed for 60 days after inoculation of the leukemia cells and their survivals were compared with that of control animals which received the same tumor inoculation and treated with filtered physiological saline. The results are shown in Table 1 where T/C(%) values are determined by dividing the mean survival time of the treated mice by that of the control mice, the quotient so obtained being multiplied by 100. The survival time of the mice which survived more than 60 days after tumor inoculation was scored as 60 days. An increase on the T/C(%) indicates an increase in the antitumor activity of the compound.

The compounds of present invention proved to be less toxic than doxorubicin hydrochloride in that doxorubicin hydrochloride showed significant decrease in T/C(%) at the dose of 16 mg/kg compared with T/C(%) at the dose of 8 mg/kg, whereas the compounds of present invention exhibited no such toxicity. As shown in Table 1, most of the compounds of present invention turned out to have superior antitumor activity to that of doxorubicin hydrochloride. Moreover, the compound of Example 3 cured all tumored mice at the doses of 32 mg/kg, 16 mg/kg, and 8 mg/kg.

TABLE 1

Antitumor activity of the compounds of present invention on L1210 murine leukemia in comparison with doxorubicin hydrochloride

| Compound | Dose (mg/kg) | T/C (%) |
|---|---|---|
| Doxorubicin Hydrochloride | 16.000 | 109 |
|  | 8.000 | 303 |
|  | 4.000 | 469 |
|  | 2.000 | 242 |
|  | 1.000 | 242 |
|  | 0.500 | 218 |
|  | 0.250 | 170 |
|  | 0.125 | 141 |
| Example 3 | 32.000 | 727 |
|  | 16.000 | 727 |
|  | 8.000 | 727 |
|  | 4.000 | 279 |
|  | 2.000 | 255 |
|  | 1.000 | 230 |
|  | 0.500 | 328 |
|  | 0.250 | 238 |
|  | 0.125 | 186 |
| Example 5 | 32.000 | 542 |
|  | 16.000 | 636 |
|  | 8.000 | 500 |
|  | 4.000 | 333 |
|  | 2.000 | 361 |
|  | 1.000 | 248 |
|  | 0.500 | 189 |
|  | 0.250 | 162 |
|  | 0.125 | 140 |
| Example 7 | 32.000 | 663 |
|  | 16.000 | 441 |
|  | 8.000 | 367 |
|  | 4.000 | 348 |
|  | 2.000 | 329 |
|  | 1.000 | 242 |
|  | 0.500 | 168 |
|  | 0.250 | 122 |
|  | 0.125 | 111 |
| Example 9 | 32.000 | 727 |
|  | 16.000 | 660 |
|  | 8.000 | 488 |
|  | 4.000 | 468 |
|  | 2.000 | 356 |
|  | 1.000 | 287 |
|  | 0.500 | 244 |
|  | 0.250 | 190 |
|  | 0.125 | 171 |
| Example 11 | 32.000 | 252 |
|  | 16.000 | 727 |
|  | 8.000 | 586 |
|  | 4.000 | 559 |
|  | 2.000 | 492 |
|  | 1.000 | 298 |
|  | 0.500 | 226 |
|  | 0.250 | 168 |
|  | 0.125 | 150 |
| Example 13 | 32.000 | 525 |
|  | 16.000 | 635 |
|  | 8.000 | 427 |
|  | 4.000 | 283 |
|  | 2.000 | 367 |
|  | 1.000 | 313 |
|  | 0.500 | 213 |
|  | 0.250 | 159 |
|  | 0.125 | 140 |
| Saline | — | 100 |

Experiment 2

In vitro growth inhibition activity of the compounds of present invention on L1210 murine leukemia cells was assessed by tetrazolium-based colorimetric assay described in Cancer Research Vol. 47, pp. 936–942, February 1987 with some modifications.

L1210 murine leukemia cells in exponential phase were plated at the density of $1 \times 10^5$ cells per well in 96-well microliter plates. The cell culture medium was RPMI 1640 (Roswell Park Memorial Institutes 1640) medium supplemented with 10% heat inactivated fetal bovine serum (FBS), 2mM L-glutamine, penicillin G sodium (100 units per ml of medium), and steptomycin sulfate (1 mg per ml of medium). The anthracycline compounds of present invention and doxorubicin hydrochloride were added to give final concentrations from 1 ng per ml to 300 ng per ml, while the control contained no drug.

The cells were incubated for 72 hours at 37.C. in an atmosphere of 10% CO and 90% air. At the end of drug exposure, 50 $\mu$l MTT(3-(4,5-dimethylthiazol-2-yl)-2,5-diphenyltetrazolium bromide) solution (2 mg per ml in phosphate-buffered saline) was added to each well and cultures were incubated at 37° C. for 4 hours in $CO_2$ incubator. The MTT is reduced to water insoluble MTT formazan(1-(4,5-dimethylthiazol-2-yl)-3,5-diphenylformazan) by mitochondrial succinate dehydrogenase only in living cells. At the end of incubation, 200 $\mu$l of supernatant was removed and the MTT formazan crystal was dissolved by adding 200 $\mu$l dimethylsulfoxide with mixing them.

The plates were then read immediately at 540 nm on a scanning multiwell spectrophotometer (enzyme-linked immunosorbent assay reader; Biotech Instruments Inc., Burlington, VT). The absorbance value corrected against uninoculated blank values. The absorbance values are directly proportional to the cell numbers in living state. The IC 50 defined a 50% reduction of absorbance against untreated control were calculated from dose-response curve and are shown in Table 2.

As shown in Table 2, all test compounds of present invention but the compound of example 7 turned out to be more cytotoxic than doxorubicin hydrochloride against L1210 murine leukemia cells.

TABLE 2

In vitro cytotoxicity of the compounds of present invention on L1210 murine leukemia cells

| Compound | IC50 (ng/ml) |
|---|---|
| Doxorubicin hydrochloride | 37.3 |
| Example 3 | 13.4 |
| Example 5 | 10.1 |
| Example 7 | 74.5 |
| Example 9 | 14.3 |
| Example 11 | 15.5 |

TABLE 2-continued

In vitro cytotoxicity of the compounds of present invention on L1210 murine leukemia cells

| Compound | IC50 (ng/ml) |
| --- | --- |
| Example 13 | 16.3 |

The invention being thus described, it will be obvious that the same may be varied in many ways. Such variations are not to be regarded as a departure from the spirit and scope of the invention, and all such modifications as would be obvious to one skilled in the art are intended to be included in the scope of the following claims.

What is claimed is:

1. A compound of the following formula (I):

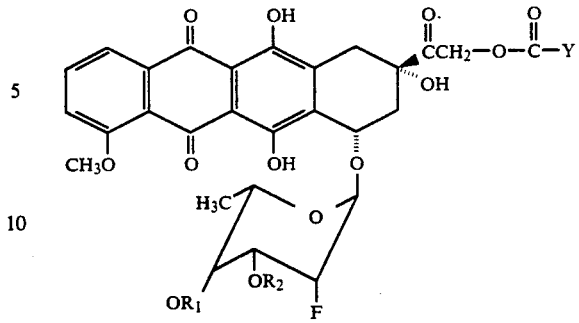

wherein Y represents

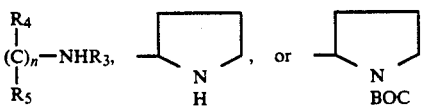

and wherein $R_1$ and $R_2$ represent hydrogen atoms, respectively, or a straight or branch chain alkylidene group having 1-10 carbon atoms; $R_3$ represents a hydrogen atom, a straight or branch chain alkyl group having 1-10 carbon atoms, or a straight or branch chain alkyloxycarbonyl group having 1-10 carbon atoms; $R_4$ and $R_5$ represent a hydrogen atom or an alkyl group having 1-5 carbon atoms, respectively; BOC represents t-butyloxycarbonyl; and n represents an integer of 0 to 10, or a pharmaceutically acceptable salt thereof.

* * * * *

UNITED STATES PATENT AND TRADEMARK OFFICE
CERTIFICATE OF CORRECTION

PATENT NO. : 5,220,001
DATED : June 15, 1993
INVENTOR(S) : Kwang D. OK, Jeong B. PARK and Moon S. KIM It is certified that error appears in the above-indentified patent and that said Letters Patent is hereby corrected as shown below:

On the title page, item [73]: Assignee:" change "Zaidan Hojim Biseibutsu Dong-A Pharm Co., Seoul, Rep. of Korea; Kagaku Kenkyukai, Tokyo, Japan" to --Dong-A Pharm., Co., Ltd., Seoul, Rep. of Korea; Zaidan Hojin Biseibutsu Kagaku Kenkyukai, Tokyo, Japan--.

Signed and Sealed this

Thirtieth Day of December, 1997

*Attest:*

BRUCE LEHMAN

*Attesting Officer*    Commissioner of Patents and Trademarks